United States Patent [19]

Newkirk

[11] Patent Number: 4,474,569
[45] Date of Patent: Oct. 2, 1984

[54] ANTENATAL SHUNT

[75] Inventor: John B. Newkirk, Evergreen, Colo.

[73] Assignee: Denver Surgical Developments, Inc., Evergreen, Colo.

[21] Appl. No.: 392,872

[22] Filed: Jun. 28, 1982

[51] Int. Cl.³ .......................................... A61M 25/00
[52] U.S. Cl. ........................................ 604/8; 604/9; 604/247
[58] Field of Search ............... 604/8, 9, 10, 891, 171, 604/247, 51, 164, 175

[56] References Cited

U.S. PATENT DOCUMENTS

| 3,540,451 | 11/1970 | Zeman | 604/8 X |
| 3,788,327 | 1/1974 | Donowitz et al. | 604/9 X |
| 4,134,405 | 1/1979 | Smit | 604/8 X |
| 4,240,434 | 12/1980 | Newkirk | 604/9 |
| 4,311,148 | 1/1982 | Courtney et al. | 604/175 |
| 4,349,023 | 9/1982 | Gross | 604/164 |
| 4,382,445 | 5/1983 | Sommers | 604/8 |

Primary Examiner—Edward M. Coven
Attorney, Agent, or Firm—James E. Pittenger

[57] ABSTRACT

An antenatal shunt is provided for implantation in utero to drain blocked fluid cavities within a fetus. The shunt includes a proximal catheter having one or more expandable wing anchors strategically positioned on the catheter, a distal tube having an additional anchor and a retracting tab provided at the free end of the distal tube. A check-valve may be provided in the catheter to allow fluid to flow in only one direction through the shunt. The shunt is sized and arranged to be implanted by means of a hollow surgical needle into the fetus by the use of ultrasonography as a guidance aid. Suitable apertures are provided in the proximal and distal free ends of the shunt to allow the flow of fluid from the fluid cavity in the fetus to the amniotic sac. Expandable anchors are included which are capable of being folded for insertion and movement through the needle during implantation. The arms expand upon release from the needle to provide a secure anchoring arrangement. The antenatal shunts provided in the present invention can be utilized for various fetal abnormalities such as antenatal hydrocephalus or a blocked urinary condition.

3 Claims, 14 Drawing Figures

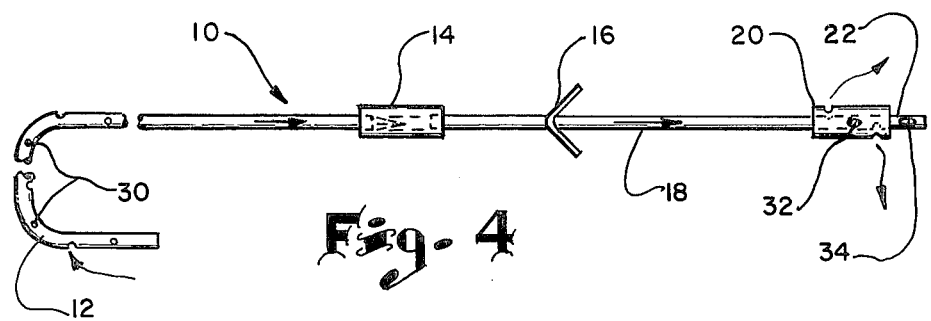
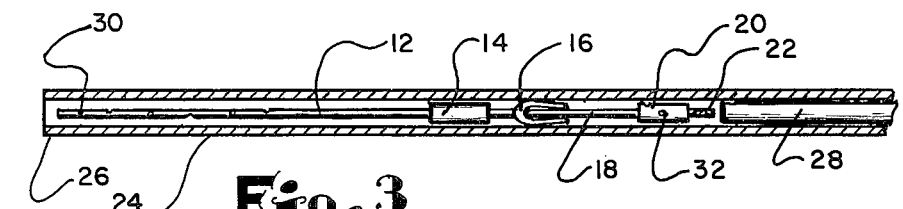
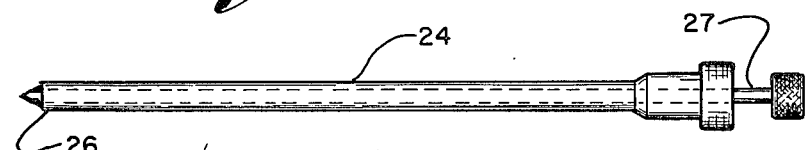
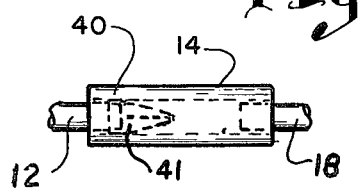
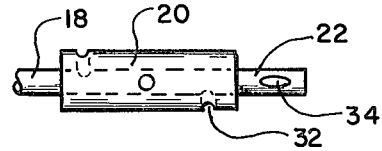
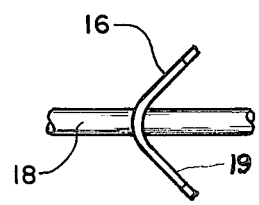
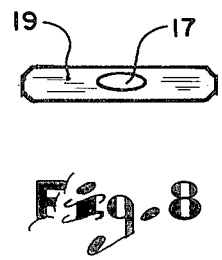

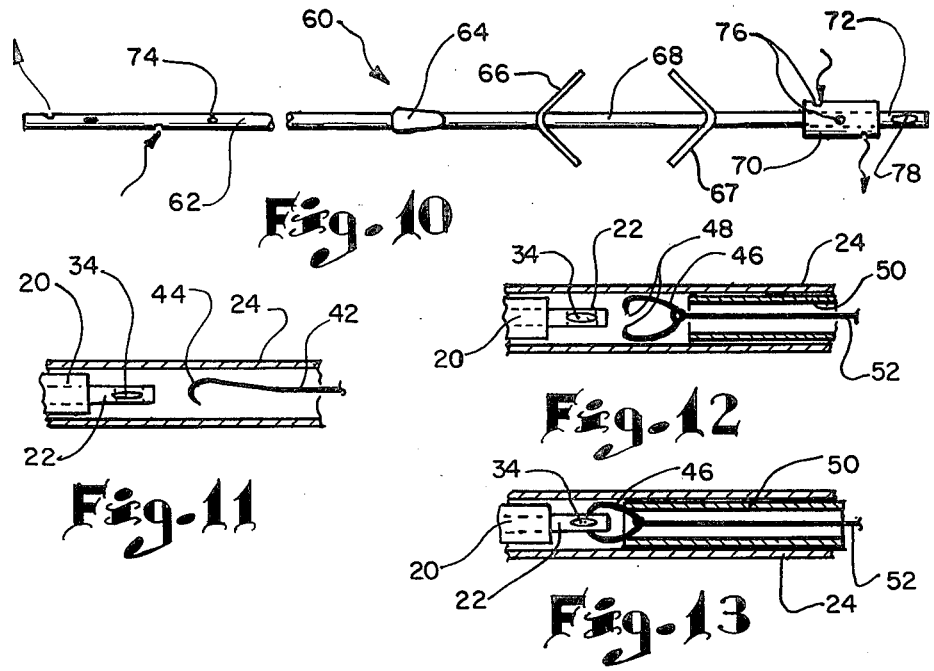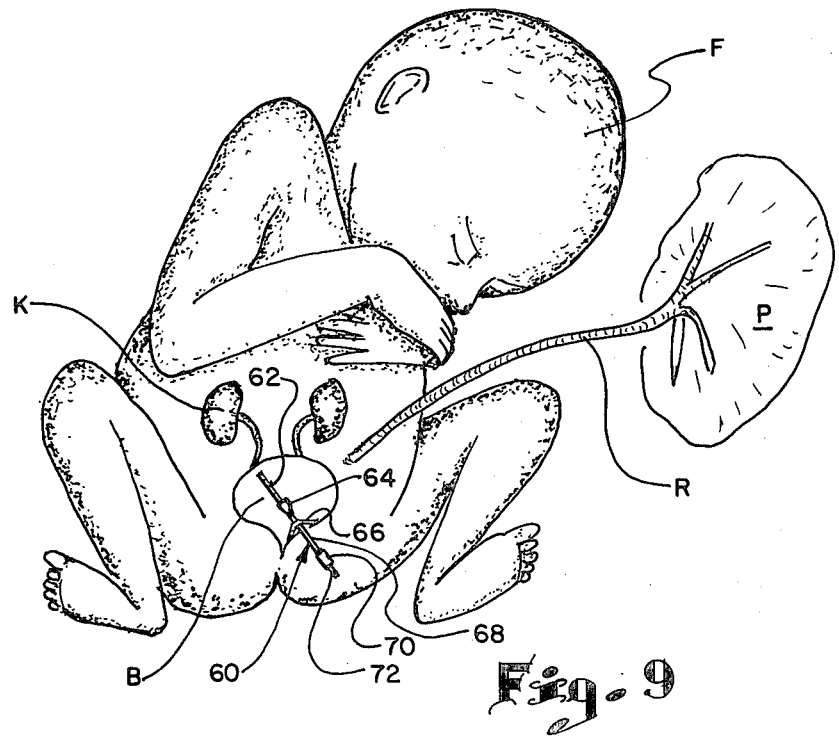

ANTENATAL SHUNT

FIELD OF THE INVENTION

This invention is directed to a micro-shunt for correcting abnormalities in a fetus while still in place in the mother's womb. It is more specifically directed to a miniature shunt which is inserted into a fetus by use of a hollow needle. The shunt includes expandable anchors which prevent dislodgement of the shunt after placement in the fetus.

BACKGROUND OF THE INVENTION

In the past the human fetus has for many years remained a medical mystery while existing in its mother's womb. Now fetal anatomy, normal and abnormal, can be accurately defined by a process called ultrasonography. This investigative process uses ultra-high frequency sound waves which are passed through the mother and fetus with return echos displayed on a cathrode ray tube showing the internal component structures of the bodies.

Until recently, the only question raised by any prenatal diagnosis of a fetal malformation was whether to abort the fetus or allow it to proceed full term with possible malformity. In some cases where these malformations are recognized too late for safe abortion, the only alternative is to provide appropriate postnatal management upon birth.

With the innovation of ultrasonography and the further development of this process to its present high level, it is now possible to recognize fetal hydrocephalus much more frequently because the fluid-filled cavities are particularly easy to detect by this method. A rather simple lesion which obstructs the passage of fluid from ducts in vital portions of the fetus can produce devastating pressures that can dilate various organs or cavities. This excess fluid pressure and dilation can greatly restrict the normal development of critical organs. One of these malformities is obstructive hydrocephalus secondary to stenosis of the aquaduct of Sylvius. In this abnormal situation the restriction of the flow of fluids from the ventricles within the brain of the fetus can produce pressures that dilate the ventricles, compress and thereby restrict the development of the brain and eventually destroy neurological function.

By the same token a urinary tract malformation and/or obstruction can produce a similar situation in the bladder of the fetus. This condition can cause consequential restriction of the development of the renal and pulmonary systems of the fetus.

In the past, it has been common clinical practice to utilize implanted shunts in adults and children for bypassing a buildup of fluid and fluid pressure from one area of the body to another. In dealing with a fetus, however, use of this type of shunt has been impossible due to its small size. This procedure is greatly complicated by the fact that accessibility to the fetus and the implantation of such a shunt is extremely tenuous. As can be visualized, it is quite difficult to merely miniaturize existing biological shunts in order to attempt to correct the abnormalities which have now been recognized in fetuses. One of the major problems involves the placement of the shunt without creating trauma in the mother or fetus which might cause termination of the pregnancy. One of the best ways found to accomplish this is by the use of a relatively small surgical needle to implant the shunt in the required area of the fetus. However, the use of this needle creates many problems relating not only to size but the actual structure of the shunt which can be implanted by needle.

In addition, many of the problems associated with this field exist because of (1) the inaccessibility of the fetus while in utero, and (2) the inability to completely diagnose the abnormality and to control the implantation of a suitable shunt. The shunt must not only be fail-proof and reliable but capable of fully performing the desired bypassing function. With the shunt installed in the fetus a continuous fluid decompression and prevention of further accumulation is provided which allows a normal growth and development of the body organs and proper development of the nervous system.

The antenatal shunt provided in the present invention addresses these major problem areas and avoids or minimizes some of the antenatal abnormalities which have been very destructive to fetuses in the past.

PRIOR ART STATEMENT

The antenatal shunt to which the present invention is directed is so new that no other direct prior art is known to exist. The prior art cited herein lists the various types of surgical drains for shunting fluids in postnatal humans which have been granted to the present applicant. These are some of the patents which are known which directly or indirectly relate to the present invention and are provided herein in compliance with the applicant's duty to provide examples of prior art which is believed to be pertinent to this invention.

The patent to John B. Newkirk, et al., U.S. Pat. No. 3,654,932, shows a hydrocephalus shunt which shows a subcutaneous pump which is characterized by a one-way slit valve which can be distorted or opened by finger pressure on the body of the valve. The body of the pump includes projections extending outwardly from either side which may be sewed to soft tissue to hold the device in position.

The John B. Newkirk patent, U.S. Pat. No. 4,037,604 shows a shunt-type drainage device for implantation in an eye for communicating the anterior chamber of the eye with the intrascleral space. In this way, excess aqueous humor within the eye can move through the valve thereby relieving excess pressure. Lateral side arms are provided as a fixation device to hold the valve in place within the eye tissue.

The patent to Arenberg, et al., U.S. Pat. No. 4,175,563, provides a body fluid drainage shunt for implantation in the inner ear. This shunt includes a pair of flaps made of flexible material. The flaps form an open cover over the end of the housing and valve to provide protection against tissue ingrowth, thereby avoiding blockage that would otherwise occur.

The patent issued to John B. Newkirk, U.S. Pat. No. 4,240,434 also shows a shunt having a perforated inlet catheter with an asymmetrical, one-way valve internally provided within a pump body. A plurality of x-ray absorbing markers are provided along the inlet and outlet catheters for ascertaining positioning of the device within the patient. The asymmetrical valve provides a continuous cleaning function during operation of the valve.

SUMMARY OF THE INVENTION

The present invention is directed to an antenatal drain for shunting fluid from a fetus, usually into the amniotic sac of the mother. This type of device is commonly called a "shunt" and will be referred to in this manner throughout this application. The shunt according to the present arrangement is intended for implantation in utero. This is to say, that the shunt, according to the present invention, must be of small diameter which will pass easily through a small diameter hollow surgical needle. In this way the shunt can be strategically implanted through the mother's abdominal wall, uterus and amniotic sac prior to being inserted into the fetus. Because we are dealing with a micro-shunt a number of new and difficult problems exist in this area.

The antenatal shunt according to this invention includes a thin-walled hollow elongated tube usually fabricated from silicone rubber and has an outside diameter of only approximately 0.047 inches. A combination of enlarged portions and expandable wing-type anchors are provided for anchoring the shunt in proper location. Where it is necessary to control fluid flow in only one direction to safeguard the integrity of the cavity being drained a suitable one-way or check valve is provided within the shunt.

If the device is intended for treating a hydrocephalic condition, the shunt is inserted through the fetal skull so that accumulated fluid can be drained from one of the ventricles within the brain into the cavity formed within the amniotic sac surrounding the fetus. Thus, for this purpose the shunt can have an overall length of between 15 to 20 centimeters, with the actual length of the catheter end determined by the surgeon implanting the shunt in accordance with the size of the fetus. Where the shunt is intended for use in relieving pressure within the bladder of the fetus due to blockage of the urinary tract it can be considerably shorter due to the fact that the bladder is close to the abdominal wall of the fetus. Usually in this application a one-way valve is unnecessary since the fluid in the bladder and in the amniotic sac are substantially the same.

The shunt according to the present invention is intended to pass through a hollow surgical needle. A size #13 surgical needle has been found to be suitable for this purpose. An expandable wing-type anchor is attached to the body of the shunt at the required location along its length, depending upon the thickness of the brain through which the shunt will be implanted. Holes are provided through the lateral surfaces of the tube near the proximal end and are spaced away from the expandable wing anchor to prevent tube blockage due to tissue ingrowth of one or more holes after implantation. The expandable wing-type anchor is important to this invention due to its expandable feature which greatly increases the projected anchoring area while in use. In addition, this same anchor can be folded back on the shunt as it is inserted into the surgical needle and is held in this position until the shunt exits from the needle during the implantation procedure. An enlarged end portion or barrel anchor also anchors the shunt in proper position. Additional holes are provided in the outer surface of the barrel anchor to allow fluid to exit freely from the distal end of the shunt which is located in the amniotic sac.

To aid in the implantation of the shunt a short section of tubing called a retracting tab extends beyond the barrel anchor approximately one to three millimeters. This tab can have several holes extending diametrically through the tab and circumferentially spaced approximately 90°. A clasp-type gripping retracter can be provided which will pass through the needle with a draw wire causing the jaws to grip the tab if it is found necessary to reposition or withdraw the shunt into the needle during the implantation process. In addition, it is also possible to use a simple thin wire hook which can be inserted through the needle to engage the holes provided in the tab. This construction feature also permits complete retraction of the shunt if an anchor has not exited the needle and entered the dilated cavity.

With respect to the antenatal shunt or any other shunt device it is possible to provide a plurality of expandable wing anchors along the body of the shunt. These anchors are strategically located along the longitudinal axis of the shunt at the proper location for anchoring the shunt in its desired position. Where a plurality of the wing anchors are used, these anchors will normally be angularly offset an equal amount. Thus, where two anchors are used they will be oriented circumferentially at right angles to each other. If a one-way valve is required as part of the shunt, it can be fabricated in accordance with the arrangements previously discussed in my U.S. Pat. Nos. 3,654,932 and 4,240,434. These patents disclose the slit-type valve as well as an asymmetrical valve arrangement which allows the valve to be self-cleaning during use. Either of these arrangements will work satisfactorily in the shunt according to the present invention.

The antenatal shunt device provided in this application can be fabricated from any suitable material including medical grade silicone rubber such as that marketed under the name "Silastic". The various components of the shunt can be joined together with medical grade adhesive such as Dow-Corning Medical Adhesive "A". The barrel anchors are formed from sections of larger sized tubing of the same material while the wing anchors can be cut from soft yet relatively rigid silicone rubber sheet material. It is to be understood that any other material which is used in the fabrication of the shunt according to the present invention must be fabricated from biocompatible materials which are suitable for this purpose.

BRIEF DESCRIPTION OF THE DRAWINGS

These and other objects and advantages of the present invention will be readily apparent by referring to the following description and appended drawings in which like reference characters represent the identical features.

FIG. 3 is a partial cross-sectional view showing the shunt positioned within the needle during implantation;

FIG. 3A is a partial cross-sectional view showing the piercing stylet positioned within the surgical needle;

FIG. 4 is a side view of the hydrocephalus shunt according to the present invention;

FIG. 5 is an enlarged cross-sectional view of the check-valve;

FIG. 6 is an enlarged cross-sectional view of the barrel anchor;

FIG. 7 is a side view of the wing anchor according to the present invention;

FIG. 8 is a plan view of the wing anchor prior to installation on the shunt;

FIG. 9 is a pictorial illustration of the antenatal bladder shunt according to the present invention implanted within the bladder of a fetus;

FIG. 10 shows a side view of the antenatal bladder shunt;

FIG. 11 shows the shunt tab and hook type retracter;

FIG. 12 is a cross-sectional view showing the shunt gripping retracter in the open position; and FIG. 13 is a cross-sectional view showing the gripping retracter engaged with the shunt tab for retracting.

DETAILED DESCRIPTION OF THE INVENTION

Figure 1:
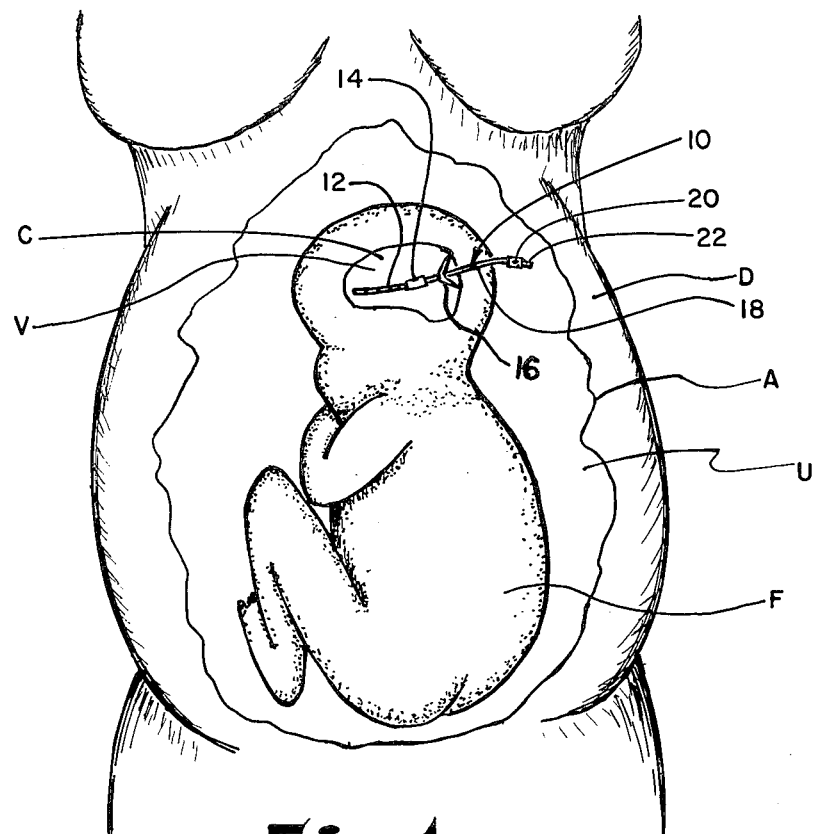
FIG. 1 is a diagramatic illustration of the fetus within the mother's womb showing the implanted antenatal hydrocephalus shunt according to the present invention.
Figure 2:
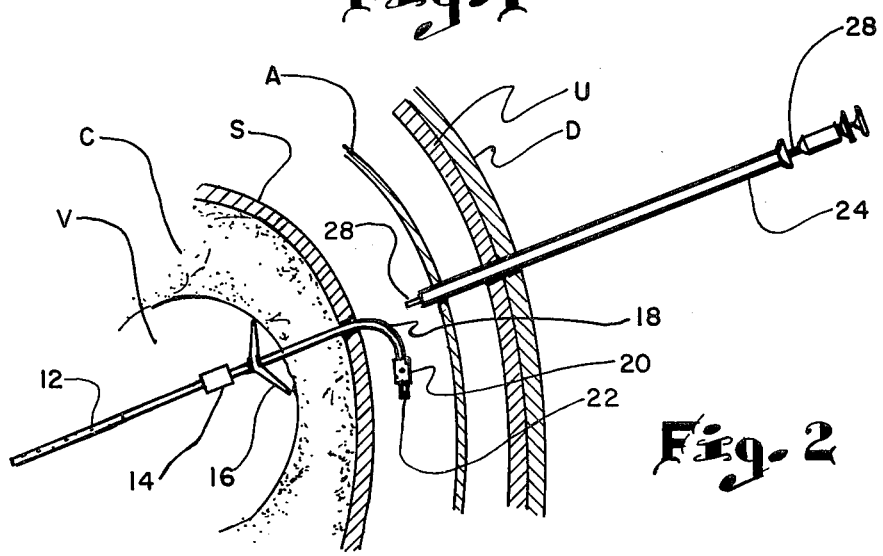
FIG. 2 is an enlarged cross-section showing a surgical needle after inserting the shunt into the ventricle of the fetus.

Turning now more specifically to the drawings, FIG. 1 is a pictorial illustration of a fetus F within the uterus U in the mother's body D. The brain of the fetus contains the lateral ventricles V which exist within the skull. As a result of some anatomic abnormality, excess fluid accumulates within the ventricular system causing increased pressure and swelling of the skull of the fetus. The antenatal hydrocephalus shunt 10 according to the present invention is shown implanted through the skull of the fetus F so that the shunt will drain fluid from the ventricle V to the amniotic sac A surrounding the fetus within the uterus. Thus, the shunt 10 allows the fluid within the ventricle to pass into the amniotic sac.

The shunt 10 includes the ventricular or proximal catheter 12, one-way valve assembly 14 allowing the fluid to flow only out of the ventricle, expandable wing anchor 16 positioned within the skull of the fetus to prevent the shunt from being displaced outwardly from the skull, distal or exit tube 18 and barrel anchor 20. The barrel anchor 20 is provided to prevent the shunt from being dislodged so that the distal end of the shunt could move into the ventricle of the fetus. Entry apertures 30 are provided in the proximal catheter 12 while exit apertures 32 are provided in the barrel anchor 20. These apertures are provided to permit continuous flow of the excess fluid from within the ventricle to the amniotic sac. A retrieval tab 22 is provided at the distal end of the barrel 20 and is provided with apertures 34 which are arranged 90° to each other and extend completely through the tab so as to provide four openings in the circumference.

For implantation of the shunt into the fetus a straight hollow surgical needle 24 having a squarely cut front end is utilized. It has been found that a Number 13 surgical needle is suitable for this purpose. A straight stylet 27, with conically sharpened point which extends beyond the squarely cut end of the hollow needle, is held firmly inside the hollow needle. The piercing pair is advanced through the mother's body and into the fetal ventricle, using ultrasonographic guidance. By proper placement and arrangement of the fetus the point 26 is manipulated so as to pierce the desired location in the skull S of the fetus.

Once entrance has been made through the skull S and excess fluid pressure has been released the shunt 10 is inserted into the open end of the needle 24 and moved downwardly through the needle by a blunt stylet 28. As the shunt 10 is inserted into the rear entrance of the needle the expandable wing anchor 16 is collapsed along the surface of the distal tube 18 so as to fit within the needle. The stylet moves the shunt longitudinally through the needle until the proximal catheter 12 is positioned within the ventricle of the fetus to a point where the wing anchor 16 is positioned on the inside of the brain. As the wing anchor 16 exits through the end 26 of the needle 24 the folded wings expand outwardly preventing the shunt from being retracted through the skull. With the blunt stylet 28 held in place against the tab 22 the hollow needle is withdrawn longitudinally from around the outside of the shunt leaving the distal tube 18 and barrel anchor 20 suspended in the amniotic sac A. At this point the hollow needle 24 and blunt stylet 28 are withdrawn from the abdominal tissue and the wound is closed.

In fabrication of the shunt 10 according to the present invention the use of suitable silicone rubber surgical tubing having an outside diameter of approximately 0.047 inches as well as an inside diameter of approximately 0.025 inches has been found to be suitable for this purpose. As shown in FIG. 5, the distal catheter 18 and the proximal tube or catheter 12 are joined together by a short section of slightly larger tubing 40 having an outside diameter of approximately 0.077 inches. The inside diameter of the tubing 40 is the same or slightly larger than the outside diameter of the catheter 12 and tube 18. These two tubes are adhered at their ends to the outer tube body 40 to form a liquid-tight unit. The end of the tube 12 that is within the outer tube 40 can be closed by a suitable adhesive and a single or pair of slits can be formed in the end of the catheter tube 12 to form the required one-way valve assembly 14.

As an alternative, as described in one of my previously referenced patents, a symmetrical or an asymmetrical one-way miter valve 41 can be formed and joined to the end of the distal catheter 12 to provide the necessary valve function. In the asymmetrical configuration two strips of silicone rubber are cut from sheet material and joined along their longitudinal sides. To provide the asymmetrical self-cleaning function of the valve 41 either the end of the proximal catheter tube 12 can be cut at an acute angle to the tube axis, or one of the strips joined together to form the valve can be of a slightly thicker material than the other. Either way the valve 41 which functioning forms a sliding action which produces the self-cleaning function. One end of the joined strips is fixed to the end of the proximal catheter 12 prior to being inserted within the body tube 40 of the valve assembly 14. The other end of the strips is left unattached to allow the flow of fluid in the desired direction. In this manner, the valve provides the restrictive function which prevents the amniotic fluid from returning through the shunt into the ventricle of the fetus.

The barrel anchor 20 is formed in a similar manner to the valve outer tube 40 except that the tube 18 is sheathed or enclosed by the larger tube forming the body of the barrel anchor 20. The tab 22 is formed by allowing the tube 18 to extend beyond the distal end of the anchor 20. A suitable adhesive is provided on each end of the anchor body 20 to securely fasten the body to the tube. In this way the tab 22 is formed and provides a gripping member for retrieving or repositioning the shunt prior to final placement within the skull. A number of apertures 32 are provided within the barrel anchor 20 and usually are staggered in various angular positions around the circumference of the anchor to allow free flow of the fluid from the distal tube 18. The body of the check valve assembly 14 and the barrel anchor 20 usually have a length within the range of 5 to 6 millimeters.

The expanding angular wing anchor 16 is cut in an elongated strip arrangement 19 as shown in FIG. 8. An oval hole 17 is cut in the center portion of the strip 19 and distal tube 18 is threaded through the opening 17 in a direction so that the outer wings of the anchor 16 are laid back toward the distal end of the shunt. The strip 19 is then affixed by a suitable adhesive to the outer surface of the tube 18. The oval configuration of the opening 17 provided within the body strip 19 causes the wings to curve slightly in one direction providing the necessary bias to hold the wings in the extended position. With this arrangement, the wings, while held against the tube 18 during passage through the implanting needle 24, extend outwardly automatically to the position shown in FIG. 7 upon being released from the needle. In this way the outwardly biased wings provide an enlarged projection area and are angularly directed toward the skull to provide greater biasing strength in the wings to substantially increase the opposition to withdrawal of the shunt from the skull. The fluid apertures 30 are spaced longitudinally from the expanding anchor to avoid ingrowth of brain or other tissue into the holes. Without this spacing it has been found that cell growth can enter one or more of the apertures 30 and cause shunt blockage during the growth and development of the internal organs.

During use and placement of the shunt 10 it has been found that it is beneficial to provide an arrangement for retracting or repositioning the shunt within the needle prior to final placement. Thus, in order to facilitate placement the distal catheter and valve 14 can be drawn back into the needle so long as the wing anchor has not exited from the end of the needle. As shown in FIG. 11 a simple wire retracter 42 having a bent end or hook 44 can be inserted through the needle and suitably manipulated so that the hook 44 will engage the retraction openings 34. This is a rather delicate maneuver which requires considerable dexterity in order to be able to hook the apertures 34.

Another arrangement can be provided which is more easily manipulated. As shown in FIGS. 12 and 13, a spring wire clamp or gripper 46 bent so as to have jaws 48 can be positioned at the mouth of an elongated thin retracting tube 50. At an intermediate location on the gripper 46 a draw wire 52 is attached and threaded outwardly through the retracting tube 50. In order to grip the tab 22 it is merely necessary to insert the retractor tube 50 until it reaches the end of retracting tab 22 on the end of the shunt 10. At this point the draw wire 52 is pulled slightly through the retracting tube 50 which causes the edge of the tube to slide against the side of the jaws 48 causing the jaws to close around and grip the tab 22. In this way, by pulling or pushing the retracting tube 50 the shunt can be repositioned within the body of the needle. Once the shunt has been repositioned the tension on the wire 52 can be relaxed and the tube slightly withdrawn so as to relieve the pressure on the jaws 48. After this has been accomplished the retracter tube 50 can be removed from the needle and the stylet again inserted so as to properly discharge the shunt.

In FIGS. 9 and 10 are shown another embodiment of the antenatal shunt which is considered part of this invention. In this arrangement the fetus is shown connected by an umbilical cord R to the placenta P. In this illustration the uterus has been omitted but it is to be understood that the fetus is still within the amniotic sac. The kidneys K and bladder B of the fetus is also diagramatically shown.

Through ultrasonography it is relatively easy to detect a situation where excess fluid is accumulating possibly in the bladder or kidney because of a urethral obstruction which can be caused by a simple lesion in the urinary duct. This type of abnormality can have catastrophic consequences on the fetal organ development. It is mandatory that the fluid pressure be relieved as quickly as possible and permanently to allow normal development of the internal organs to proceed prior to birth. This condition can also be corrected in utero by the sonagraphically guided percutaneous techniques which have been described above.

In this procedure the antenatal shunt is implanted through the surgical needle through the abdominal wall and uterus of the mother with the needle pair also piercing the abdominal wall and bladder of the fetus. This procedure is accomplished identically to the arrangement previously described above for the hydrocephalus shunt. In this way the urine within the bladder is prevented from building up pressure and is continuously discharged into the amniotic sac without deleterious effect on the kidneys.

In the arrangement shown in FIG. 9 the shunt 60 is shown with the proximal or entry catheter 62 and expanded wing anchors 64, 66 positioned within the bladder B of the fetus F. The distal or exit catheter 68, barrel anchor 70 and retracting tab 72 are shown extending outwardly through the bladder and abdominal wall of the fetus into the amniotic sac. Since the amniotic fluid within the sac is very similar to the fluid within the bladder it is immaterial whether the amniotic fluid can reverse flow into the bladder. For this reason the check-valve previously described is unnecessary in this embodiment. As shown in FIG. 10, apertures 74 are provided in the proximal catheter 62 and additional apertures 76 are provided in the barrel anchor 70 as well as the retracting apertures 78 provided within the retracting tab 72.

In the arrangement described herein for the urinary shunt 60, a pair of expanding angled wing anchors 64, 66 are shown. These anchors are illustrated as being arranged 90° to each other to provide additional projection to prevent the shunt from exiting through the wall of the bladder and abdomin. It is to be understood that any number of wing anchors can be provided as a safeguard to prevent the shunt from being withdrawn through the wall of the bladder. By the same token, it is also to be understood that one or more additional wing anchors can be positioned in the opposite direction and spacedly arranged longitudinally along the distal tube. Those anchors can be provided either, instead of or in addition to, the barrel anchors previously described. In this way it is possible to have expanding angled wing anchors positioned on both sides of the bladder and abdominal wall of the fetus to prevent the shunt from inadvertently becoming dislodged from the bladder in either direction. In this way the shunt is securely positioned.

In the application described herein for relieving urinary pressures within the fetal bladder the shunt 60 can have shorter dimensions than the hydrocephalus shunt previously described. The major consideration to be given to the overall outside diameter of the shunt is the size of the needle which is to be utilized for implanting the shunt in utero. The number and position of the expandable anchors which can be utilized on a shunt of this type are dependant upon the intended purpose and the anatomy involved.

While an improved antenatal shunt has been shown and described in detail, it is to be understood that this

What is claimed is:

1. An antenatal micro-shunt for complete implantation inutero in a fetus by use of a thin-hollow surgical needle, so that a blocked fluid cavity within the fetus can be continuously drained, said shunt comprising:
 a thin body tube fabricated from a flexible material and having an internal fluid passageway, said tube having an outside diameter small enough to pass freely through the interior of said surgical implanting needle;
 the proximal and distal ends of said tube each having at least one aperture formed diametrically through the tube to allow the entrance of the fluid to the internal passageway;
 two or more anchors are attached to the body of said tube, at least one of said anchors is attached near the distal end of the tube while at least one other anchor is attached to a portion generally near the midpoint of said tube;
 at least one of the anchors near the midpoint of said tube has angularly positioned expandable arms wherein when said shunt is being implanted through said needle the arms are folded against the body of the tube to allow it to pass freely through the needle and to expand in an outwardly direction forming an acute angle with the body of the tube when the anchor clears the end of the needle whereby the anchor can be placed on one side of the membrane forming the cavity to be drained with the arms angled toward the membrane while the distal end anchor attached thereto prevents the tube from passing through the membrane in the opposite direction;
 said angled arm anchor is formed from a single strip of thin, flexible material having an oval aperture formed near the midpoint of said strip, the tube being threaded through the aperture of said strip and the strip being permanently affixed to the outside of said tube, the narrowest dimension of said oval aperture being sized slightly smaller than the outside diameter of the tube so that the ends of the strip are biased in the same direction to form an acute angle with the longitudinal axis of the tube; and
 at least one of the anchors formed near the distal end of said tube is an enlarged sleeve mounted on the outer surface of the tube, said sleeve having an outside diameter sufficient to restrict the inward movement of said tube into said cavity while at the same time being smaller than the inside diameter of said needle to allow said implantation.

2. An antenatal shunt as described in claim 1, wherein:
 at least one of the anchors near the distal end of the tube is an expandable anchor with the arms arranged to expand angularly outward from said tube to form an acute angle in a direction toward the midpoint expandable anchor whereby the expandable arm anchors can be positioned on either side of the membrane of the cavity to be drained to prevent dislodgement of the body tube in either direction.

3. An antenatal shunt as described in claim 1, which further includes:
 a valve for restricting the fluid flow through the tube in only one direction whereby the fluid will exit from the blocked cavity and through the distal end of said tube.

* * * * *